United States Patent [19]

Willis et al.

[11] Patent Number: 5,322,360
[45] Date of Patent: Jun. 21, 1994

[54] ISOTHERMAL CALORIMETER

[75] Inventors: Peter M. Willis, Benton Harbor; Gordon C. Ford, St. Joseph; Michael P. Tabbey, St. Joseph; Charles W. Berk, St. Joseph, all of Mich.

[73] Assignee: Leco Corporation, St. Joseph, Mich.

[21] Appl. No.: 26,870

[22] Filed: Mar. 5, 1993

[51] Int. Cl.$^5$ .................. G01K 17/10; G01N 25/16
[52] U.S. Cl. ................................. 374/38; 364/557
[58] Field of Search ........................... 374/38, 33, 36

[56] References Cited

U.S. PATENT DOCUMENTS

| | | |
|---|---|---|
| 550,943 | 12/1895 | Carpenter . |
| 1,103,915 | 7/1914 | Junkers . |
| 1,247,998 | 11/1917 | Parr . |
| 3,285,053 | 11/1966 | Maziers . |
| 3,456,490 | 7/1969 | Stone . |
| 3,593,577 | 7/1971 | Monner . |
| 3,599,666 | 8/1971 | Curtis et al. . |
| 3,650,306 | 3/1972 | Lancaster . |
| 3,789,662 | 2/1974 | Zettler et al. . |
| 3,978,325 | 8/1976 | Goldstein et al. . |
| 4,398,836 | 8/1983 | Sitek . |
| 4,616,938 | 10/1986 | Bonnard ............................ 374/38 |

FOREIGN PATENT DOCUMENTS

| | | |
|---|---|---|
| 238395 | 5/1910 | Fed. Rep. of Germany . |
| 2840595 | 4/1979 | Fed. Rep. of Germany . |
| 571218 | 12/1975 | Switzerland . |

OTHER PUBLICATIONS

"Precision Isoperibol Calorimeter with Automatic Data Acquisition and Processing," C. Shin et al., Review of Scientific Instruments, American Institute of Physics, vol. 46, No. 8, pp. 1043-1046, Aug. 1975.
"New Design of a Vacuum Jacket Precision Combustion Calorimeter," P. B. Arrken et al., The Review of Scientific Instruments, vol. 25, No. 10, Oct. 1954, pp. 967-970 (author unknown).
"Standard Test Method for Gross Calorific Value of Solid Fuel by the Isothermal Jacket Bomb Calorimeter," American National Standard ANSI/SSTM D3286-77, American Society for Testing & Materials, published Dec. 1977, pp. 1-10 (author unknown).
"Determination of the Gross Calorific Value of the Bomb Calorimeter and Calculation of the Net Calorific Value, Method Using Isothermal Water Jacket," DIN 51-900-German Standards (DIN-Normen), Aug. 1977, pp. 1-8 (author unknown).
"Heat of Combustion of Hydrocarbon Fuels by Bomb Calorimeter (High-Precision Method)," American Society for Testing & Materials, ANSI/ASTM D-23-82-76, published Sep. 1976, pp. 1-12 (author unknown).

Primary Examiner—Daniel M. Yasich
Attorney, Agent, or Firm—Price Heneveld Cooper DeWitt & Litton

[57] ABSTRACT

A calorimeter for determining the calorific value of a sample on the basis of the difference in temperature, measured on a real time basis, between the temperature of the water in a bucket containing the sample in a conventional calorimeter bomb and the temperature of the water in a reservoir maintained at substantially ambient temperature. The water from the reservoir is circulated by a pump through a heat exchanger, a water jacket surrounding the bucket and back to the reservoir in an effort to maintain the water in the system at ambient temperature. A method for calculating the corrected bucket temperature rise on the basis of Newton's Law of Cooling and for calculating the gross calorific value of the sample is also disclosed.

14 Claims, 4 Drawing Sheets

ISOTHERMAL CALORIMETER

BACKGROUND OF THE INVENTION

In accordance with a standard method for determining the calorific value of a solid fuel sample recommended by the American National Standard Institute, ANSI/ASTM D 3286-77, a complicated apparatus is employed which requires careful control and maintenance of temperatures in a water "jacket and in the calorimeter vessel in which the combustion bomb is immersed in water. It is not uncommon for such equipment to require water heaters, water coolers along with several valves and pumps to maintain the temperature and the recommended difference in temperature between the calorimeter vessel and the water jacket before the sample can be combusted. It is also recommended that the equipment be set up and used in a special draft free room which is maintained at a constant temperature and that the water in the calorimeter vessel surrounding the bomb be one or more degrees below the ambient water temperature of the water in the water jacket. This adds a further complication in maintaining the temperature difference before the sample is combusted.

In order to determine the calorific value of the sample, the heat given up by the combustion bomb, due to the complete combustion of the sample in an oxygen atmosphere, is equal to the temperature increases of the water in the calorimeter vessel when properly corrected for the heat capacity of the calorimeter and for heat transfer losses. The most common formula used to determine the correct temperature change in the bucket containing the bomb is that developed by Regnault-Pfaundler in 1866. This formula requires that the temperature of the water surrounding the bomb be carefully monitored for several minutes before the sample is combusted to determine when the rate of change of temperature of the water has become constant. At this time the sample can be combusted in the bomb which causes the water temperature about the bomb to rise. The temperature must again be monitored carefully to determine when the temperature has gone through its peak and has begun to cool at a constant rate. The determination of the constant rate of temperature change both before and after the sample burn is critical to the calculation. Precise determination of the rate of change of the temperature requires careful, periodic temperature measurements over several minutes in order to accurately measure each rate of change. It can be seen from the above that the standard process for determining the calorific value of a sample requires a special room, a complicated assembly of equipment and a extended period of time to precisely measure the temperatures in order to determine the rate of change of the temperature which is critical to the final calculation.

SUMMARY OF THE INVENTION

In accordance with the present invention, an improved apparatus and method has been developed for determining the calorific value of a sample which is substantially simpler and more accurate than those systems currently used. Temperature data received from both calorimeter vessel, or commonly referred to as the bucket, and the water jacket are monitored on a real time basis. This data, combined with prior knowledge of a temperature dependent cooling constant (k), is then used to determine the heat transfer corrections for the system. No assumptions are made. The ability to measure bucket temperature and ambient/jacket temperature simultaneously allow the system to simply track ambient temperature. The system requires none of the elaborate equipment previously required to maintain a constant jacket temperature.

These and other advantages, purposes and features of the invention will become more apparent from a study of the following description taken in conjunction with the drawing figures described below.

DETAILED DESCRIPTION OF THE PREFERRED EMBODIMENTS

Figure 1:
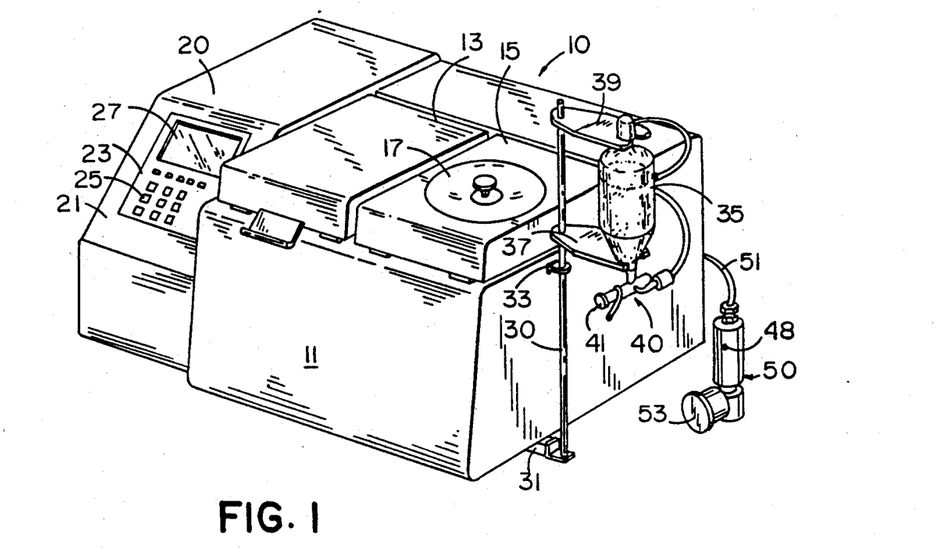
FIG. 1 is a perspective view of the calorimeter.

Referring to FIG. 1, the isothermal calorimeter is indicated generally by the number 10. The calorimeter has an outer cover 11 having pivotally mounted covers 13 and 15. Cover 13 is for the water jacket and the calorimeter bucket while cover 15 covers the bulk water storage reservoir. Cover 15 has a removably center cover 17 covering an access port to water storage reservoir. At the left end of the calorimeter, as shown in FIG. 1, is a subcabinet 20 which has a sloping front face 21 upon which is mounted a panel 23 which includes a digital keypad 25 for entering appropriate data necessary to conduct the calorimeter experiment. Above keypad 25 is a digital display 27 upon which input and output data can be shown. At the opposite end of the calorimeter is a stand 30 which is attached to the bottom of the calorimeter by an angular foot 31. A clamp 33 surrounds an upper portion of stand 30 to keep the stand stabilized against the side of cabinet 11. A volumetric pipette 35 is supported by a lower clamp 37 which grips the lower shaped portion of the pipette and an upper clamp 39 which grips the upper portion and stabilizes the pipette. A control valve 40 has a finger operated handle 41 which controls the filling and emptying of pipette 35.

A conventional combustion bomb (not shown) is used with apparatus 10 and, after having a weighed sample added thereto, is filled with several atmospheres pressure of pure oxygen. For this purpose an oxygen valve 50 is provided which is connected to an oxygen supply by a tube 51. A finger operated switch 48 controls the filling of the combusticn bomb with oxygen. The pressure is monitored using gauge 53.

Figure 2:
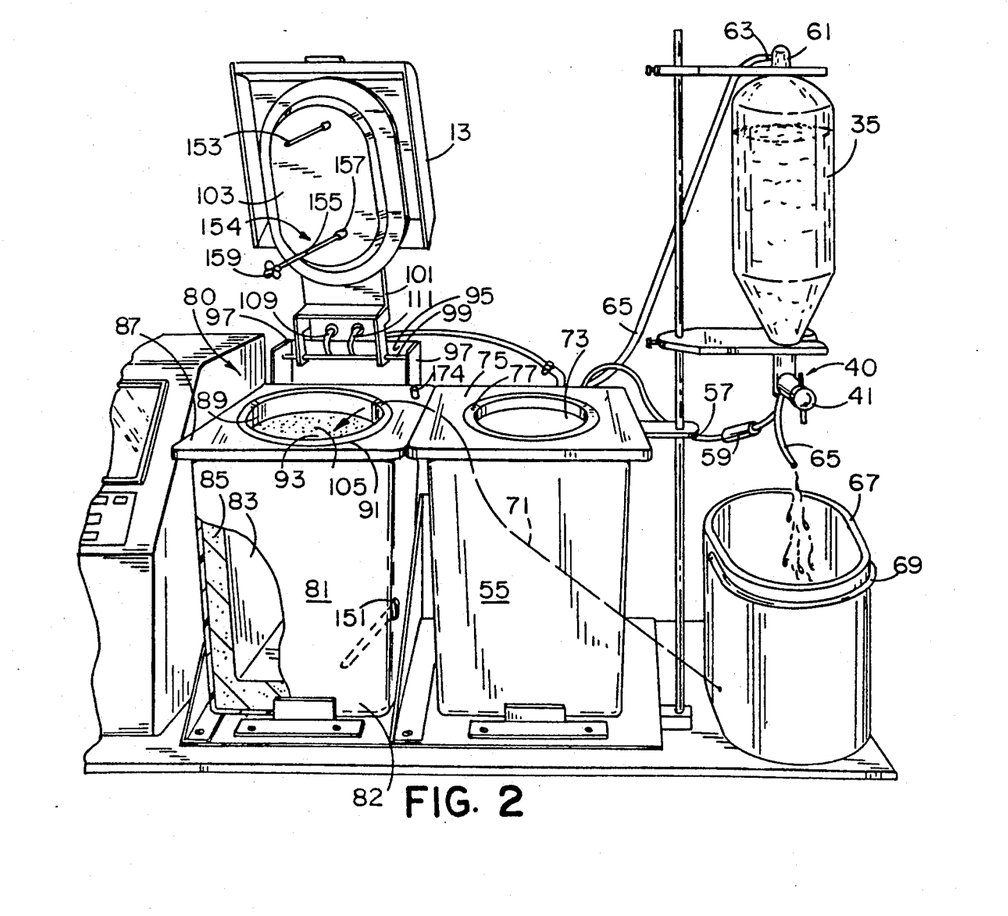
FIG. 2 is a front elevational view, with some covers removed, showing the reservoir and water jacket with cover open.

Now referring to FIG. 2, the calorimeter is shown with outer cover 11 and reservoir cover 17 removed.

The calorimeter has a reservoir 55 which can be made of molded plastic which contains the bulk quantity of water used in the operation of the system. Water is taken from reservoir 55 through flexible tubular conduit 57 and water filter 59 to control valve 40. By the proper manipulation of finger operated valve 41, volumetric pipette 35 can be filled with precisely 2,000 milliliters of water. The water can be caused to flow in and up through the bottom and, when the proper amount is reached, the overflow 61 causes the excess water to pass through a nipple 63 into flexible tubing 65 where the water returns to reservoir 55. After the water is measured, finger valve 41 can be turned to cause the water to flow from spigot 65 into bucket 67.

Bucket 67 is preferably made of a highly polished metal such as a stainless steel of the 400 series which can have a high surface polish. The bucket has a handle 69 to provide for the easy handling of the bucket when prepared with the combustion bomb (not shown) and the 2,000 milliliters of water. As shown by dashed arrow 71, the bucket water and combustion bomb are positioned within the calorimeter. At the end of the experiment, the water in bucket 67 can be poured through opening 73 in top 75 of the reservoir to return the water to bulk water reservoir 55. Aperture 73 in cover 75 is lined with a protective edge 77. Cover 75 and edge 77 can be made of any suitable plastic materials. The plastic material also helps to retain the temperature of the water in reservoir 55.

Figure 4:
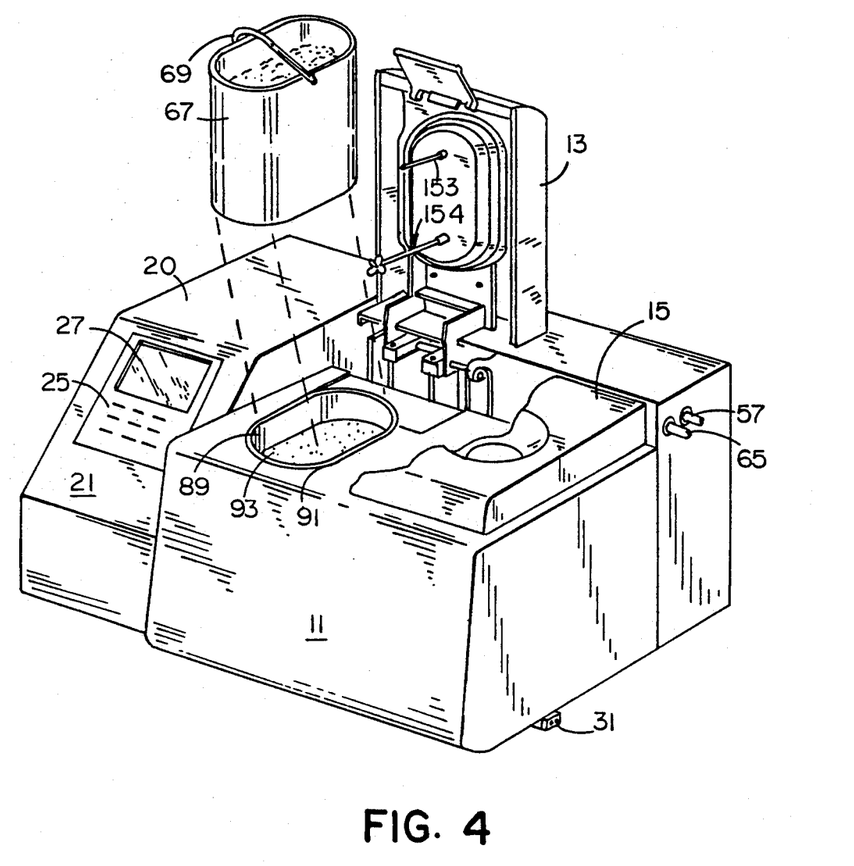
FIG. 4 is an exploded perspective view showing the calorimeter bucket above the water jacket.

When a calorimeter experiment is to be run, bucket 67 can be suspended from handle 69 and moved to and inserted into a calorimeter 80. Calorimeter 80 has a water jacket 81 formed by an outer wall 82 and an inner wall 83, between which water 85 from reservoir 55 is caused to circulate. Water jacket 81 has a plastic lid 87 which supports a highly polished metal vessel 89 by a turned rim 91. Vessel 89 has a lining, approximately one-quarter inch in thickness, of a plastic foam material 93 to help stabilize the heat transfer from bucket 67 to vessel 89.

On the back of calorimeter 80 is a lid 95 which has spaced vertical legs 97 which support a pivot rod 99. Cover 13 is attached to a metal hinge member 101 which is mounted on pivot rod 99.

Figure 5:
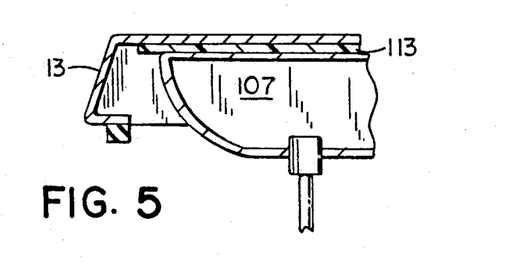
FIG. 5 is a partial sectional view of the lid for the water jacket.

Supported within cover 13 is a lid 103 configured to fit within the opening 105 of vessel 89. Referring to FIG. 5, lid 103 is hollow and has an internal water chamber 107 in which water from reservoir 55 can circulate. Conduit 109 supplies water to lid 103 while conduit 111 (FIG. 2) returns the water to the reservoir. By circulating water through lid 103 a continuous water jacket surrounds the calorimeter during an experiment. In order to further isolate the water jacket from possible heat transfer losses, a sheet of plastic material 113 is placed between lid 103 and cover 13.

Figure 3:
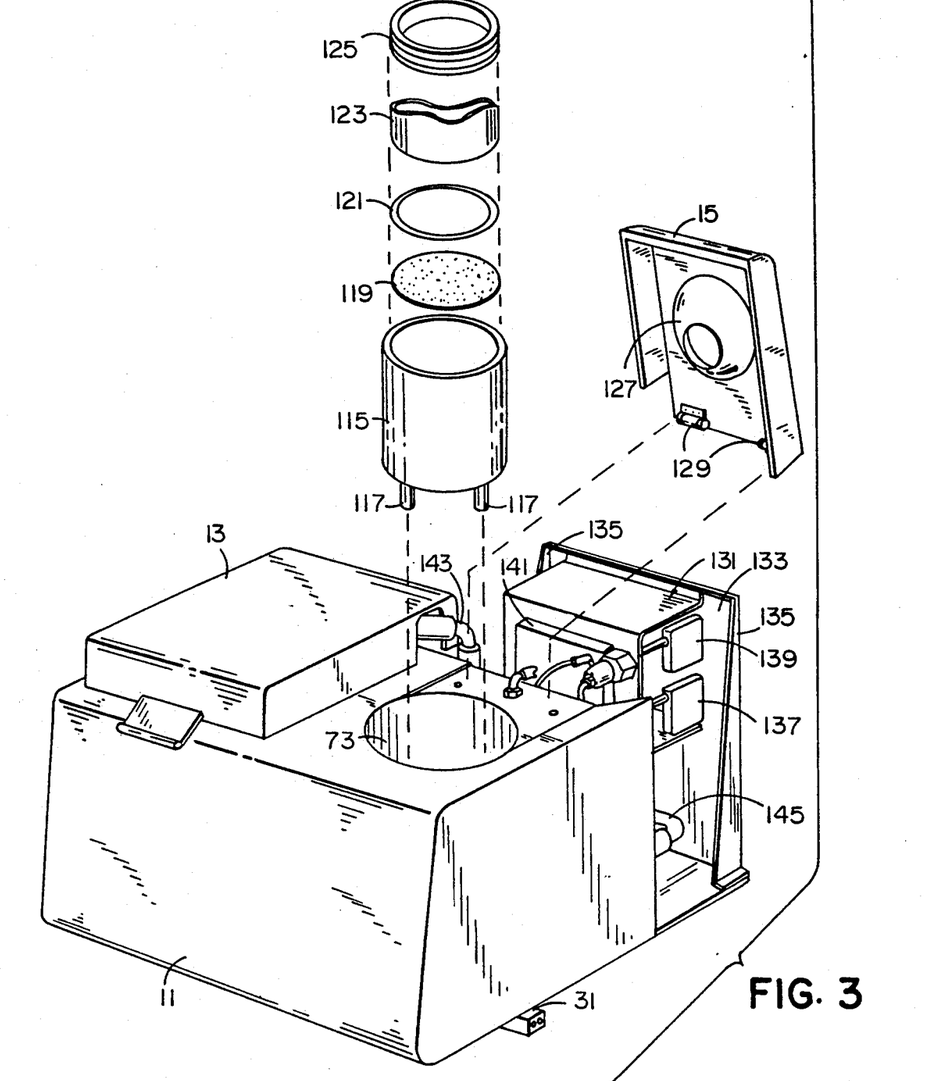
FIG. 3 is an exploded perspective view of the calorimeter, with some covers removed showing the filter support for the reservoir and the heat exchanger.

A significant aspect of the present invention is that a single water supply, maintained at ambient temperature, is used for the entire isothermal calorimeter system. Referring to FIG. 3, reservoir 55 is used to contain the water and, as mentioned above, after a sample is run, the bucket is poured back into reservoir 55. Within reservoir 55 is positioned a filter subassembly 115 which is supported from the bottom of the reservoir by spaced legs 117. A screen 119 covers the bottom of the subassembly and is held in place by a seal member 121. A filter media 123, such as a piece of filter paper, or a filter from an automatic coffee percolator, is positioned in the subassembly and held in place by a locking ring 125.

Filter 123 and screen 119 protect the water pump and water circulation system of the calorimeter from any foreign substance.

Reservoir lid 15 has a tapered funnel-shaped guide member 127 which fits within the upper portion of filter subassembly 115 to direct water poured back into the reservoir. Cover 15 is pivotally attached to the top of cabinet 11 by a pair of spaced hinges 129.

It is very important to the operation of the isothermal calorimeter that the water circulating from the reservoir through the water jacket and lid be at ambient temperature. To assist in maintaining the water at ambient temperature, a heat exchanger 131 is mounted on a vertical support panel 133 at the rear of the calorimeter. Support panel 133 has a pair of spaced triangularly-shaped legs 135 which reinforce panel 133 and help to support the weight of heat exchanger 131. Water enters heat exchanger 131 through a lower fitting 137 and exits and returns to the reservoir through an upper fitting 139. The heat exchanger has a core similar to a radiator core upon which air is blown by an internal electric fan 141 through an air filter (not shown).

Figure 6:
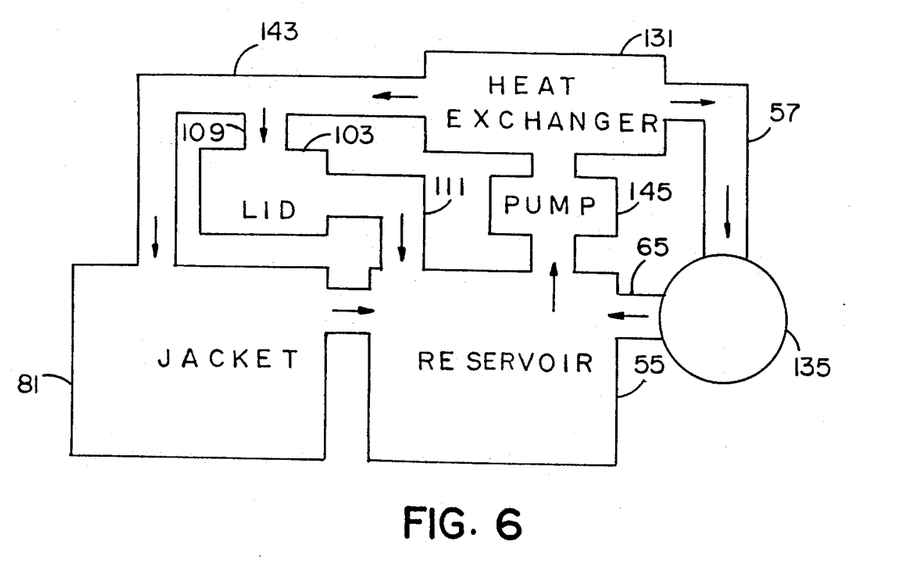
FIG. 6 is a schematic diagram illustrating the water flow in the calorimeter.

The isothermal calorimeter uses a single pump 145 (FIG. 6) to circulate water from the reservoir into heat exchanger 131. The water then exits the heat exchanger and flow through conduit 57 to volumetric pipette 135, and then back through conduit 65 to reservoir 55. The water can also exit the heat exchanger through conduit 143 and 109 and enter chamber 107 in lid 103 from which it can return to the reservoir through conduit 111. The water from the heat exchanger can also flow directly to water jacket 81 and, again, back to reservoir 55. It can be clearly seen from an examination of FIG. 6 that the water in the entire system is circulated by pump 145 through all of the major components of the calorimeter. Heat exchanger 131 effectively maintains the calorimeter at the ambient temperature of the room in which the apparatus is operating without the need for a closed, temperature controlled, draft-free room. The calorimeter is intended to operate over an ambient temperature range of 15° to 35° C.

As discussed above, the water in the entire system is circulated by pump 145 through the several components of the calorimeter. The temperature of the water from resevoir 55 within water jacket 81 is monitored by a thermister 151 (FIG. 2). Thermister 151 is positioned adjacent the water inlet (not shown) to jacket 81. A similar thermister 153 extends through lid 103 and, when cover 13 is closed, is immersed in the water surrounding the combustion bomb in bucket 67. In order to have a uniform temperature throughout the bucket, a stirrer 154 is used to circulate the water. Stirrer 154 has a shaft 155 extends through a collar 107 in lid 103. Stirring shaft 155 with a stirring blade 159 affixed to the end thereof for moving the water in the bucket so that the uniform temperature can be quickly and evenly reached.

Figure 8:
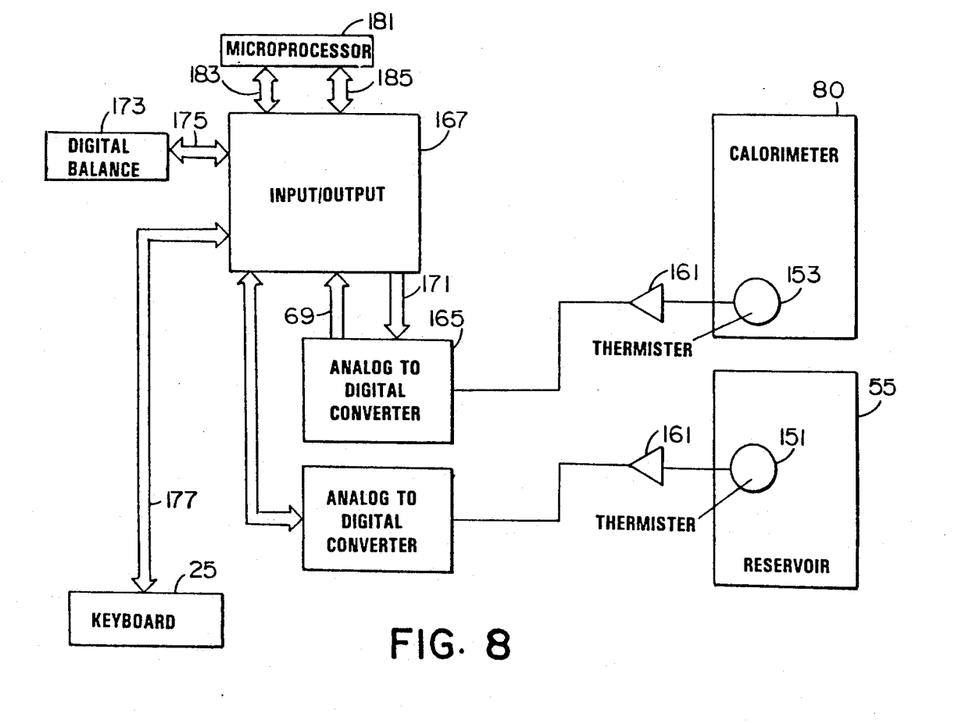
FIG. 8 is a schematic, in block diagram form, of the electronic control for the calorimeter.

Turning now to FIG. 8, the electronic circuitry for the isothermal calorimeter is illustrated. Calorimeter vessel 80 has a thermister 153 for monitoring the temperature of the water in bucket 67. A similar thermister 151 is provided for monitoring the temperature of the water in the jacket from reservoir 55. While thermisters are the preferred temperature measuring devices, other devices capable of producing an analog or digital output signal can be used. The output of each of the thermisters is sent through its own preamplifier 161 to its own analog to digital converter 165 which converts the analog signals from each of the thermisters into digital signals which are transmitted to an input/output device 167 over digital data bus 169. Control signals for the analog to digital converter are sent over a data bus 171 from the input/output device. A digital balance 173, for weighing the sample to be placed in the combustion bomb, is coupled to the input/output device through a data bus 175. Digital keyboard 25 and display 27 transmit and receive information to and from the input/output device through a bidirectional data bus 177. A microprocessor 181 having RAM and ROM capability is connected to input/output controller 167 by bi-directional data buses 183 and 185. In the preferred embodiment the readily available 8085 microprocessor device from Intel Corporation is used. The procedure for programming the device and its use is well documented. Other microprocessor devices of equal or greater capability from Intel and other manufacturers, such as Motorola and Texas Instruments, can also be used.

The temperature of the water in the bucket surrounding the combustion bomb and the temperature of the water in the jacket must, preferably, each be precisely measured to within 0.0001° C. Before any tests are carried out with the calorimeter, each of the thermisters and their preamplifier are carefully checked against each other at a low temperature with each preamplifier being switched between the thermisters so that any gain or offset differences can be noted. A similar comparison is made at a high temperature so that any differences in each of the thermisters and its associated preamplifier can be determined before any tests are carried out. During this calibration, thermister 153 is temporarily positioned within jacket 81 such that thermister 153 is adjacent thermister 151. Thermister 153 is positioned within jacket 81 through an opening 174 in lid 87.

In determining the calorific value of a sample, a portion is carefully weighted on digital scale 173 and the output fed over data bus 175 to input/output controller 167 into the memory of microprocessor 181. The calorimeter bomb is then prepared with a fuse wire in the normal way and is tightly sealed and filled with 400 pounds of pure oxygen by oxygen dispenser 50 The bomb is then placed in the bucket where it is supported in the center of the container. Two thousand milliliters of water are then added to the bucket from volumetric pipette 135. The bucket is then placed within container 89 in the calorimeter and lid 13 is closed. Stirrer blade 159 is then caused to rotate to circulate the water in the bucket.

Figure 7:
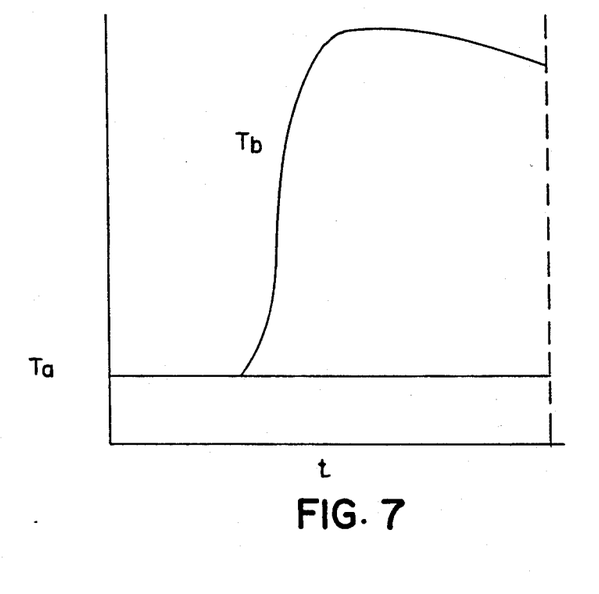
FIG. 7 is a temperature time graph showing the bucket temperature relative to the reservoir temperature.

The temperature of the water in the bucket and the temperature of the water in the jacket are both monitored at 6 second intervals, on a real time basis. After an equilibrium time of approximately 1½ to 3 minutes which time is selected by the operator, the temperature of the water in the bucket has approached a thermal equilibrium and the sample is combusted. The temperature of the water in the bucket then rises in proportion to the amount of heat given off by the sample. As shown in FIG. 7, temperature $T_a$ is the initial temperature of the water in the bucket and is equal to the temperature in the jacket. After the firing, the temperature of the water in the bucket $T_b$ rises to a peak and then begins to decrease, eventually at a uniform rate. The temperature difference between the temperature of the water in the bucket and the temperature in the water in the jacket is then used to calculate the correction factor Q by which the measured temperature is to be corrected. The corrected bucket temperature rise can be used according to conventional calorimetric techniques to determine the calorific value of the sample.

As mentioned previously, the most common formula used for calculating the correction factor Q is that derived by Regnault-Pfaundler. In order to use this formula, great care must be taken prior to the burn of the sample and after the burn of the sample to precisely determine the rate of change of the temperature of the water in the bucket. In a typical experiment, it takes approximately twenty minutes from beginning to end to determine the values to be used in the determination of the correction factor. In contrast, in using the system and technique of the present invention, the initial time period prior to the burn is reduced from several minutes to little more than one minute with the overall process of combusting the sample and determining the appropriate correction factor being carried out in approximately four to seven minutes.

In order to determine the calorific value of a sample, a known weight of the sample is burned in an atmosphere of pure oxygen to assure complete combustion. The sample and oxygen are contained in a bomb which is immersed in a known volume of water. The initial temperature of the water should be the same in the jacket and bucket since that same water was used to fill the bucket.

On combustion of the sample, the heat given off by the sample will be equal to the heat absorbed by the water which is measured by a change in temperature of the water. If the heat transfer from the bucket to the water jacket is limited, and if the amount of heat absorbed by the bomb itself is known and other heat transfer affects are taken into consideration, the change in temperature of the water in the bucket is an accurate measure of the calorific value of the sample.

In accordance with the procedure of the present invention, the temperature of the water in the bucket and the temperature of the water in the jacket are measured at predetermined times, for example, every six seconds, over the entire course of the experiment. The length of the time periods can be other than six seconds so long as both temperatures are measured at the same time and compared on a real time basis. After each measurement the bucket temperature correction Q is recalculated. Contrary to the Regnault-Pfaundler technique, measurements are not made to determine the rate of change of the temperature before and after the sample burn. The present invention is only concerned with the difference in temperature and since the jacket temperature is ambient temperature, the ambient temperature is monitored on a real time basis as any change in the ambient temperature of the room will be reflected in the jacket temperature. No attempt is made to hold the temperature of the water in the jacket at a known fixed temperature. An attempt is made, however, through the use of an air cooled heat exchanger to keep the water at ambient temperature which can, preferably, be a temperature between 15° and 35° C.

The steady-state rate of heat transfer between the calorimeter proper (bucket) and the surrounding environment (calorimeter jacket) using the isoperibol method can be expressed by Newton's cooling law:

$$q = h * (T_b - T_a) = \xi * d(T_b)/dt$$

where:

q = the heat transfer rate (Watts)

$T_b$ = the temperature of the bucket (° C.),
$T_a$ = the temperature of the jacket (° C.),
h = heat transfer coefficient (Watts/° C.),
$\xi$ = the effective heat capacity of the calorimeter (J/° C.).

This equation makes two general assumptions:
 a) the heat generated from the stirrer and thermister is negligible; and
 b) the contributions of non-steady-state heat transfer are negligible.

The first assumption is valid as long comparative experiments are performed. However, the non-steady-state conditions prevailing during the main firing period produce errors ranging from 100 to 1000 ppm depending upon the magnitude and rate of temperature increase. If no correction for this effect is made, the instrument must be calibrated with an amount of benzoic acid that will produce a temperature rise equivalent to the rise expected during the experiments. Dividing equation (1) by $\xi$ yields:

$$q/\xi = (h/\xi) * (T_b - T_a) = k * (T_b - T_a) = d(T_b)/dt$$

where:
 k = the cooling constant of the calorimeter in (second$^{-1}$).

Integrating or summing equation (2) over the main firing period yields the change in the temperature, Q, of the bucket due to heat transfer from the jacket:

$$Q = \Sigma^n (q/\xi * \Delta t)$$

where:
 Q = the temperature change of the bucket (° C.),
 $\Delta t$ = the sampling period (seconds),
 $\Sigma n$ = number of samples during the main firing period,
 $n$ = the summation from 0 to n.

Q is then subtracted from the calorimeter bucket temperature rise to yield the net temperature rise due to the sample burn alone. Substituting equation (2) into (3) results in the following equation:

$$Q = \Sigma^n (k * (T_b - T_a) * \Delta t)$$

Microprocessor 181 has equation (4) programmed therein along with a correction for the non-steady-state heat transfer which greatly improves the linearity of the instrument. Equation (4) requires prior knowledge of the temperature dependent cooling constant, k, and real time measurement of both $T_b$ and $T_a$. This heat transfer equation inherently compensates for changes in $T_a$ and prior knowledge of k allows the use of predictive algorithms to further improve precision and/or decrease the analysis time.

A series of preliminary tests should preferably be run with the calorimeter using known weights of benzoic acid, of known calorific value. The benzoic acid standard can be obtained from the National Bureau of Standards. The tests can be carried out using the techniques of the present invention and using the Regnault-Pfaundler equation to determine the correction for non-steady-state heat transfer and the cooling constant k of the calorimeter. This procedure is preferably followed with each calorimeter bomb with the resulting data stored in memory.

The above-described test should preferably be repeated over the 15° to 35° C. range of temperature and the value k plotted against ambient temperature to insure that there is a linear relationship.

Since the entire calorimeter experiment is monitored on a real time basis, the correctness of the procedure can be monitored by observing the output data. The maximum temperature difference between the bucket and the jacket, when corrected for heat loss during the burn period will provide the value of Q or bucket temperature correction needed to calculate the calorific value of the sample according to the following equation which has been programmed into the microprocessor:

$Q_v(\text{gross}) = [Q*W]/g$
 Q = corrected bucket temperature rise
 W = energy equivalent of calorimeter (a volume known from the previously described tests carried out with benzoic acid)
 g = weight of sample g.

The calorific value of the sample can then be read on the digital display and, if desired, can be printed out on a connected printer (not shown).

Although the invention has been described with respect to specific preferred embodiments thereof, many variations and modifications will become apparent to those skilled in the art. It is, therefore, the intention that the appended claims be interpreted as broadly as possible in view of the prior art to include all such variations and modification.

The embodiments of the invention in which an exclusive property or privilege is claimed as defined as follows:

1. A calorimeter comprising:
 a bucket for containing water and a calorimeter bomb;
 a water jacket surrounding said bucket for containing water at ambient temperature;
 a first temperature measuring device for measuring the temperature of the water in said bucket before, during and after a sample is combusted in the calorimeter bomb;
 a second temperature measuring device for measuring the temperature of the water in the water jacket at least after combustion of the sample is initiated; and
 computing means coupled to said first and second temperature measuring devices, said computing means for determining a corrected bucket temperature rise, attributable to the combustion of the sample, as a function of the difference in temperature between the temperature of the water in the bucket and the temperature of the water in the jacket as measured after initiation of combustion of the sample, and said computing means for calculating said corrected temperature rise based on a temperature dependent cooling constant, and said computing means for calculating the calorific value of the sample using said corrected bucket temperature.

2. The calorimeter as set forth in claim 1, including a timing means for causing said temperature measuring device in said bucket and said temperature measuring device in said jacket to measure the respective temperatures at predetermined intervals at least during the combustion of said sample.

3. The calorimeter as set forth in claim 2, wherein said timing means causes said bucket temperature and said jacket temperature to be measured at substantially the same time intervals, whereby the difference in the temperature of the bucket and the jacket is calculated based on the difference in the temperatures measured at these sampling intervals.

4. A calorimeter as set forth in claim 1, further including a lid for said water jacket, said lid having a chamber in which water can be circulated.

5. A calorimeter comprising:
a bucket for containing water and a calorimeter bomb;
a water jacket surrounding said bucket for containing water at ambient temperature;
a temperature measuring device for measuring the temperature of the water in the bucket before, during and after a sample is combusted in the calorimeter bomb; a temperature measuring device for measuring the temperature of the water in the water jacket; and
computing means for determining a corrected bucket temperature rise, attributable to the combustion of the sample, using the difference in temperature between the temperature of the water in the bucket and the temperature of the water in the jacket and a temperature dependent cooling constant and for calculating the calorific value of a sample using said corrected bucket temperature;
a reservoir for containing a supply of water;
a heat exchanger connected to said reservoir and said water jacket; and
a pump for circulating water through said water jacket, said reservoir and said heat exchanger.

6. A calorimeter as set forth in claim 5, wherein said heat exchanger has a core through which water can circulate and a fan for moving ambient air over said core to cause said water to be at substantially ambient temperature.

7. An calorimeter comprising;
a bucket for containing a known volume of water and a calorimeter bomb;
a container for receiving and supporting said bucket;
a water jacket surrounding said container;
a reservoir for containing water;
a heat exchanger connected to said reservoir;
a pump operably coupled to said reservoir, said heat exchanger, and said water jacket, said pump circulating water through said reservoir, said heat exchanger and said water jacket for maintaining said water substantially at an ambient temperature;
a first temperature measurement device for measuring the temperature of the water in said reservoir at predetermined time intervals, on a real time basis;
a second temperature measuring device for measuring the temperature of the water in the bucket at predetermined time intervals, on a real time basis, including temperature before, during and after a sample is combusted in a calorimeter bomb in said bucket;
a controller coupled to said first and second temperature measurement devices and calculating the net temperature increase of water in the bucket as a function of the difference in temperature of the water in the reservoir and the temperature of the water in the bucket measured by said first and second temperature measurement devices at least after initiation of combustion of a sample, the controller calculating the net temperature increase based on a temperature dependent cooling constant and the predetermined time intervals, and said controller calculating the calorific value of a sample combusted in a calorimeter bomb in said bucket based on said net temperature increase.

8. A calorimeter comprising:
a bucket for containing water and a colorimeter bomb;
a water jacket surrounding said bucket for containing water at ambient temperature;
a temperature measuring device for measuring the temperature of the water in the bucket before, during and after a sample is combusted in the calorimeter bomb; a temperature measuring device for measuring the temperature of the water in the water jacket; and
computing means for determining a corrected bucket temperature rise, attributable to the combustion of the sample, using the difference in temperature between the temperature of the water in the bucket and the temperature of the water in the jacket and a temperature dependent cooling constant and for calculating the calorific value of a sample using said corrected bucket temperature, wherein said water jacket has a cover to which said lid is attached, and a layer of plastic material between said cover and said lid.

9. A calorimeter comprising:
a bucket for containing water and a calorimeter bomb;
a water jacket surrounding said bucket for containing water at ambient temperature;
a temperature measuring device for measuring the temperature of the water in the bucket before, during and after a sample is combusted in the calorimeter bomb; a temperature measuring device for measuring the temperature of the water in the water jacket;
computing means for determining a corrected bucket temperature rise, attributable to the combustion of the sample, suing the difference in temperature between the temperature of the water in the bucket and the temperature of the water in the jacket and a temperature dependent cooling constant and for calculating the calorific value of a sample using said corrected bucket temperature; and
a layer of foam insulating material between said bucket and said water jacket.

10. A calorimeter comprising;
a bucket for containing water and a calorimeter bomb;
a water jacket surrounding said bucket for containing water at ambient temperature;
a temperature measuring device for measuring the temperature of the water in the bucket before, during and after a sample is combusted in the calorimeter bomb; a temperature measuring device for measuring the temperature of the water in the water jacket; and
computing means for determining a corrected bucket temperature rise, attributable to the combustion of the sample, using the difference in temperature between the temperature of the water in the bucket and the temperature of the water in the jacket and a temperature dependent cooling constant and for calculating the calorific value of a sample using said corrected bucket temperature, wherein said computing means subtracts the temperature change of the bucket due to heat transfer from the temperature change of the bucket due to the sample burn to determine the net temperature rise of the bucket.

temperature of the water in the bucket measured by said first and second temperature measurement devices at least after initiation of combustion of a sample, the controller calculating the net temperature increase based on a temperature dependent cooling constant and the predetermined time intervals, and said controller calculating the calorific value of a sample combusted in a calorimeter bomb in said bucket based on said net temperature increase.

11. A method for determining the calorific value of a combustible sample comprising the following steps:

providing a calorimeter including a water reservoir, a heat exchanger, a water jacket and a pump for circulating water through the reservoir, the heat exchanger and the water jacket;

preparing a calorimeter bomb with a known weight of sample and pressure of oxygen;

providing a bucket containing a known volume of water and positioning said calorimeter bomb in said water jacket;

measuring the temperature of said water in said bucket and said water in said jacket at predetermined times;

initiating combustion of said sample in said calorimeter bomb;

determining the temperature of said water in said bucket and said water in said jacket at time intervals after combustion is initiated;

determining the temperature change of the bucket; and computing a corrected bucket temperature change due to the sample burn as a function of the measured temperature of said water in said bucket and the measured temperature of said water in said jacket, measured at said time intervals and calculating the calorific value of a sample based on said corrected bucket temperature.

12. A method for determining the calorific value of a sample as set forth in claim 11, further including the step of passing air over said heat exchanger to cause said water to be substantially at an ambient temperature.

13. A method for determining the calorific value of a combustible sample comprising the following steps:

providing a calorimeter including a water reservoir, a heat exchanger, a water jacket and a pump for circulating water through the reservoir, the heat exchanger and the water jacket;

preparing a calorimeter bomb with a known weight of sample and pressure of oxygen;

providing a bucket containing a known volume of water and positioning said calorimeter bomb in said water jacket;

measuring the temperature of said water in said bucket and said water in said reservoir at predetermined times;

combusting said sample in said calorimeter bomb;

determining the temperature of said water in said bucket and said water in said reservoir;

determining the temperature change of the bucket; and computing a corrected bucket temperature due to the sample burn based on the temperature change of said bucket, and calculating the calorific value of a sample based on said corrected bucket temperature, wherein said corrected bucket temperature is calculated as a function of a correction factor for the bucket temperature, and said correction factor is determined from the following formula:

$$Q = \Sigma^n (k*(T_b - T_a)* \Delta)$$

where:

$Q$ = temperature change of the bucket due to that transfer from the jacket (C°):

$T_b$ = the temperature of the bucket (C°);

$T_a$ = the temperature of water in jacket (C°);

$k$ = cooling constant of the calorimeter (seconds$^{-1}$);

$\Delta t$ = a sampling period at which the temperatures of the bucket and reservoir are measured;

$\Sigma^n$ = the summation of 0 to n the correction factor Q is used to determine corrected bucket temperature.

14. The method as set forth in claim 13, wherein a net temperature rise of the bucket is determined by subtracting Q from the measured bucket temperature rise due to the sample burn.

* * * * *

UNITED STATES PATENT AND TRADEMARK OFFICE
CERTIFICATE OF CORRECTION

PATENT NO. : 5,322,360

DATED : June 21, 1994

INVENTOR(S) : Willis, et al

It is certified that error appears in the above-indentified patent and that said Letters Patent is hereby corrected as shown below:

Column 1, Line 10
  Page 1, Line 8
    Before "jacket" delete --"--.

Column 2, Line 65
  Page 4, Line 26
    "combusticn" should be --combustion--.

Column 8, Line 29
  Page 17, Line 2
    "as defined" should be --are defined--.

Column 10, Line 38
  Claim 9, Line 11 (Amend A)
    "suing" should be --using--.

Column 12, Line 29
  Claim 13, Line 21 (Amend A)
    After "$\Delta$" insert --t--.

UNITED STATES PATENT AND TRADEMARK OFFICE
CERTIFICATE OF CORRECTION

PATENT NO. : 5,322,360
DATED : June 21, 1994
INVENTOR(S) : Willis, et al

It is certified that error appears in the above-indentified patent and that said Letters Patent is hereby corrected as shown below:

Column 12, Line 32
      Claim 13, Line 23 (Amend A)
        "that" should be --heat--.

Signed and Sealed this

Twentieth Day of December, 1994

*Attest:*

BRUCE LEHMAN

*Attesting Officer*      *Commissioner of Patents and Trademarks*